(12) United States Patent
Thirumalai Rajan et al.

(10) Patent No.: US 10,093,625 B2
(45) Date of Patent: Oct. 9, 2018

(54) PROCESS FOR THE PREPARATION OF [[2(S)-[[4(R)-(3-HYDROXYPHENYL)-3(R), 4-DIMETHYL-1-PIPERIDINYL]METHYL]-1-OXO-3-PHENYLPROPYL]AMINO]ACETIC ACID DIHYDRATE

(71) Applicant: MSN LABORATORIES PRIVATE LIMITED, Hyderabad, Telangana (IN)

(72) Inventors: Srinivasan Thirumalai Rajan, Telangana (IN); Sajja Eswaraiah, Telangana (IN); Komati Satyanarayana, Telangana (IN)

(73) Assignee: MSN Laboratories Private Limited, Hyderabad, Telangana (IN)

( * ) Notice: Subject to any disclaimer, the term of this patent is extended or adjusted under 35 U.S.C. 154(b) by 0 days.

(21) Appl. No.: 15/509,786

(22) PCT Filed: Sep. 8, 2015

(86) PCT No.: PCT/IN2015/000352
§ 371 (c)(1),
(2) Date: Mar. 8, 2017

(87) PCT Pub. No.: WO2016/038622
PCT Pub. Date: Mar. 17, 2016

(65) Prior Publication Data
US 2017/0247328 A1    Aug. 31, 2017

(30) Foreign Application Priority Data

Sep. 9, 2014   (IN) .......................... 4411/CHE/2014

(51) Int. Cl.
*C07D 211/22* (2006.01)
*C07C 51/06* (2006.01)
*C07C 51/367* (2006.01)
*C07D 263/24* (2006.01)

(52) U.S. Cl.
CPC ............ *C07D 211/22* (2013.01); *C07C 51/06* (2013.01); *C07C 51/367* (2013.01); *C07D 263/24* (2013.01)

(58) Field of Classification Search
None
See application file for complete search history.

(56) References Cited

U.S. PATENT DOCUMENTS

2004/0254377 A1   12/2004  Le Bourdonnec et al.
2005/0203123 A1    9/2005  Dolle et al.

FOREIGN PATENT DOCUMENTS

WO    WO 2011/161646    12/2011

OTHER PUBLICATIONS

Kim, M.-h. et al Chem. Comm. 2009 vol. 7 pp. 782-784.*
CAPLUS 2011:853629.*
Heravi. Majid M., et al. "Oxazolidinones as Chiral Auxiliaries in Asymmetric Aldol Reactions Applied to Total Synthesis", Tetrahedron Asymmetry, vol. 24, Issue 19, Oct. 15, 2013, pp. 1149-1188.
Written Opinion of the International Searching Authority issued in International Patent Application No. PCT/IN2015/000352, dated Mar. 22, 2016.

* cited by examiner

*Primary Examiner* — Heidi L Reese
(74) *Attorney, Agent, or Firm* — Seyfarth Shaw LLP

(57) ABSTRACT

The present invention relates to an improved process for the preparation of [[2(S)-[[4(R)-(3-hydroxyphenyl)-3(R),4-dimethyl-1-piperidinyl]methyl]-1-oxo-3-phenylpropyl] amino]acetic acid dihydrate, represented by the following structural formula (I).

13 Claims, 2 Drawing Sheets

PROCESS FOR THE PREPARATION OF [[2(S)-[[4(R)-(3-HYDROXYPHENYL)-3(R), 4-DIMETHYL-1-PIPERIDINYL]METHYL]-1-OXO-3-PHENYLPROPYL]AMINO]ACETIC ACID DIHYDRATE

RELATED APPLICATIONS

This application is a national phase application under 35 U.S.C. § 371 of International Application No. PCT/IN2015/000352, filed on Sep. 8, 2015, which claims priority to Indian patent application number 4411/CHE/2014 filed on Sep. 9, 2014; the disclosures of all of which are incorporated herein by reference in their entirety.

FIELD OF THE INVENTION

The present invention relates to an improved process for the preparation of [[2(S)-[[4(R)-(3-hydroxyphenyl)-3(R),4-dimethyl-1-piperidinyl]methyl]-1-oxo-3-phenylpropyl]amino]acetic acid dihydrate, represented by the following structural formula:

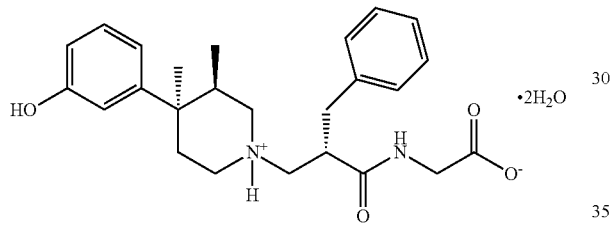

BACKGROUND OF THE INVENTION

Alvimopan dihydrate, chemically known as [[2(S)-[[4 (R)-(3-hydroxyphenyl)-3(R),4-dimethyl-1-piperidinyl]methyl]-1-oxo-3-phenylpropyl]amino]acetic acid dihydrate is indicated to accelerate the time to upper and lower gastrointestinal recovery following partial large or small bowel resection surgery with primary anastomosis.

U.S. Pat. No. 6,242,635 B1 discloses the process for the preparation of (R)-2-benzyl-3-hydroxy propanoic acid which is as follows:

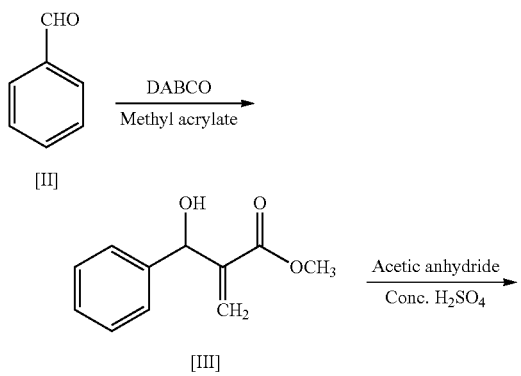

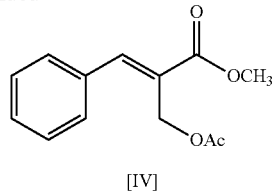

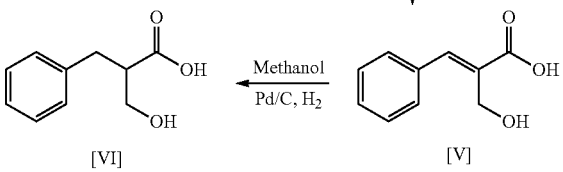

The above said process is having following disadvantages, which include:
- Process for the preparation of compound of formula-III is critical and takes place 2-3 days for completion of the reaction.
- Usage of raw material like methyl acrylate is not suggestible for use in laboratory as well as commercial scale process.
- Usage of expensive palladium-carbon for the reduction of compound of formula-V and also resulted in the formation of undesired byproduct leading to decrease in yield of desired product and increases the cost of production.
- The compound of formula-VI may require resolution to get the desired compound which may lead to the loss of unwanted enantiomer and provides the wanted enantiomer with 50% yield.

As the above said process suffers from several drawbacks including use of inaccessible raw materials, expensive reagents and involving time consuming multi-step reaction sequences, lengthy procedure for the separation of isomers mixture involving column chromatographic purification's resulting in low yield of the desired product.

Hence, there is a need in the art to develop an improved, economical viable and efficient route for the preparation of (R)-2-benzyl-3-hydroxypropanoic acid that provides good yield with high enantionmeric purity of the desired compound as well as the yield and purity of [[2(S)-[[4(R)-(3-hydroxyphenyl)-3(R),4-dimethyl-1-piperidinyl]methyl]-1-oxo-3-phenylpropyl]amino]acetic acid dihydrate.

BRIEF DESCRIPTION OF THE INVENTION

The first aspect of the present invention is to provide an improved process for the preparation of (R)-3-((S)-2-benzyl-3-hydroxypropanoyl)-4-phenyloxazolidin-2-one compound of formula-5, comprising of hydroxy methylating the (R)-4-phenyl-3-(3-phenylpropanoyl)oxazolidin-2-one compound of formula-4 with 1,3,5-trioxane in the presence of a suitable base and a suitable catalyst in a suitable solvent to provide (R)-3-((S)-2-benzyl-3-hydroxypropanoyl)-4-phenyloxazolidin-2-one compound of formula-5.

The second aspect of the present invention is to provide an improved process for the preparation of (S)-2-benzyl-3-hydroxypropanoic acid compound of formula-1, comprising of;

a) Hydroxy methylating the (R)-4-phenyl-3-(3-phenyl-propanoyl)oxazolidin-2-one compound of formula-4 with 1,3,5-trioxane in the presence of a suitable base and a suitable catalyst in a suitable solvent to provide (R)-3-((S)-2-benzyl-3-hydroxypropanoyl)-4-phenyloxazolidin-2-one compound of formula-5, b) hydrolyzing the compound of formula-5 with a suitable base in presence of hydrogen peroxide in a suitable solvent to provide (S)-2-benzyl-3-hydroxypropanoic acid compound of formula-1.

The third aspect of the present invention is to provide an improved process for the preparation of (S)-2-benzyl-3-hydroxypropanoic acid compound of formula-1 or its phenylethylamine salt compound of formula-1a, comprising of the following steps:

a) Reacting the 3-phenylpropanoic acid compound of formula-2 with (R)-4-phenyloxazolidin-2-one compound of formula-3 in presence of a suitable coupling agent and a suitable base in a suitable solvent to provide (R)-4-phenyl-3-(3-phenylpropanoyl)oxazolidin-2-one compound of formula-4, b) hydroxy methylating the (R)-4-phenyl-3-(3-phenylpropanoyl)oxazolidin-2-one compound of formula-4 with 1,3,5-trioxane in the presence of a suitable base and a suitable catalyst in a suitable solvent to provide (R)-3-((S)-2-benzyl-3-hydroxy propanoyl)-4-phenyloxazolidin-2-one compound of formula-5, c) hydrolyzing the compound of formula-5 with a suitable base in presence of hydrogen peroxide in a suitable solvent to provide (S)-2-benzyl-3-hydroxypropanoic acid compound of formula-1, d) optionally, treating the compound of formula-1 with (S)-phenyl ethylamine in a suitable solvent to provide (S)-phenyl ethylamine salt of (S)-2-benzyl-3-hydroxypropanoic acid compound of formula-1a and further converting it into compound of formula-1 by using a suitable acid in a suitable solvent.

The fourth aspect of the present invention is to provide an improved process for the preparation of (R)-4-phenyl-3-(3-phenylpropanoyl)oxazolidin-2-one compound of formula-4, comprising of reacting the 3-phenylpropanoic acid compound of formula-2 with (R)-4-phenyloxazolidin-2-one compound of formula-3 in presence of a suitable coupling agent and a suitable base in a suitable solvent to provide (R)-4-phenyl-3-(3-phenylpropanoyl) oxazolidin-2-one compound of formula-4.

The fifth aspect of the present invention is to provide an improved process for the preparation of [[2(S)-[[4(R)-(3-hydroxyphenyl)-3(R),4-dimethyl-1-piperidinyl]methyl]-1-oxo-3-phenylpropyl]amino]acetic acid dihydrate.

The sixth aspect of the present invention is to provide highly pure (S)-2-benzyl-3-hydroxypropanoic acid compound of formula-1.

The seventh aspect of the present invention relates to novel (R)-3-((S)-2-benzyl-3-hydroxypropanoyl)-4-phenyloxazolidin-2-one compound of formula-5.

The eighth aspect of the present invention is to provide an alternate process for the preparation of [[2(S)-[[4(R)-(3-hydroxyphenyl)-3(R),4-dimethyl-1-piperidinyl]methyl]-1-oxo-3-phenylpropyl]amino]acetic acid dihydrate.

DETAILED DESCRIPTION OF THE INVENTION

Figure 1:
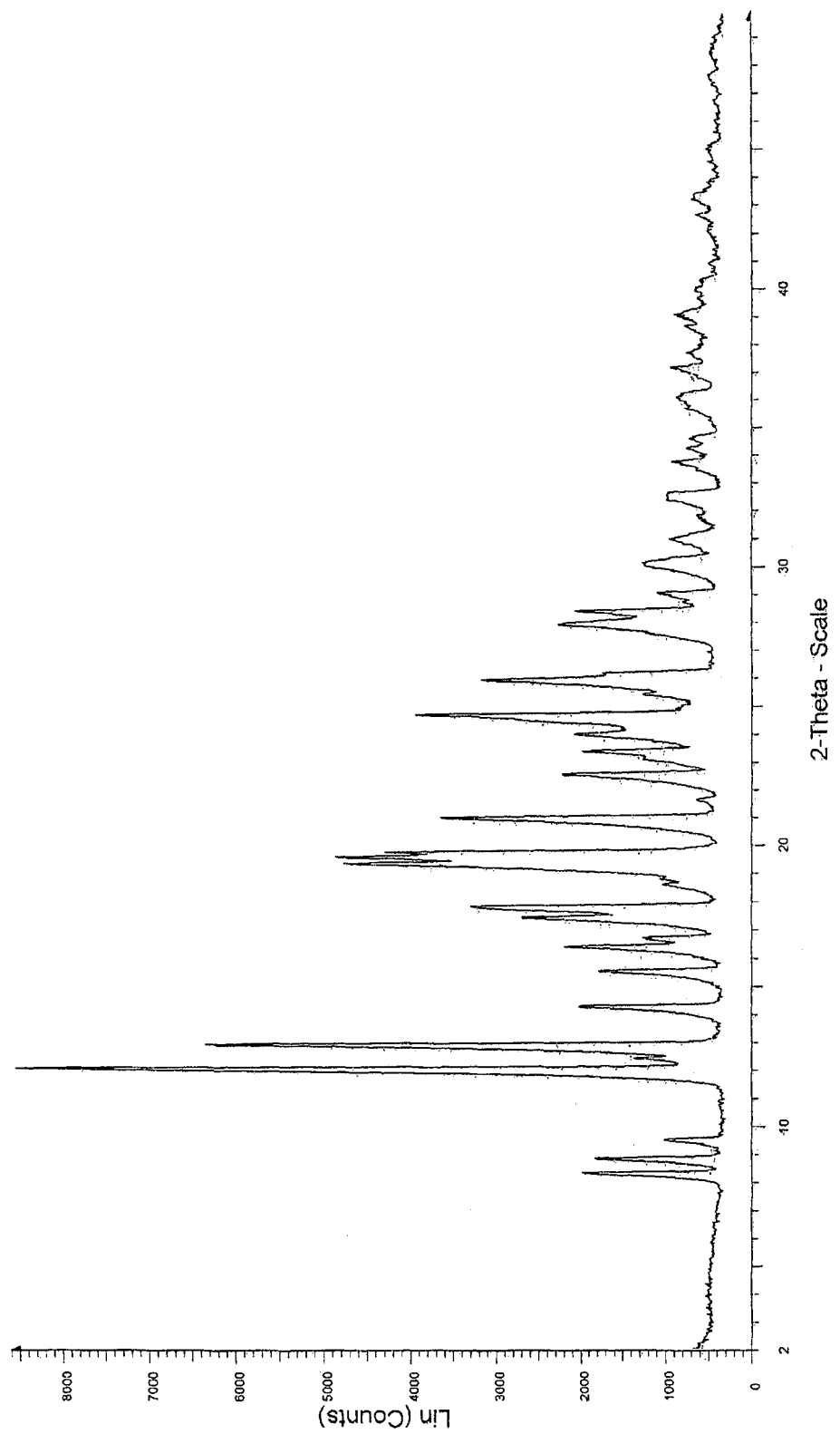
FIG. 1: Illustrates the PXRD pattern of crystalline form of [[2(S)-[[4(R)-(3-hydroxyphenyl)-3 (R),4-dimethyl-1-piperidinyl]methyl]-1-oxo-3-phenylpropyl]amino]acetic acid dihydrate.

The term "suitable solvent" used in the present invention until unless specified is selected from, but not limited to "ester solvents" such as ethyl acetate, methyl acetate, isopropyl acetate, n-butyl acetate and the like; "ether solvents" such as tetrahydrofuran, dimethyl ether, diethyl ether, diisopropyl ether, methyl tert-butyl ether, 1,4-dioxane and the like; "hydrocarbon solvents" such as toluene, hexane, heptane, pet.ether, benzene, xylene, cyclohexane and the like; "polar aprotic solvents" such as dimethyl acetamide, dimethyl sulfoxide, dimethyl formamide, N-methyl-2-pyrrolidone and the like; "ketone solvents" such as acetone, methyl ethyl ketone, methyl isobutyl ketone and the like; "alcoholic solvents" such as methanol, ethanol, n-propanol, isopropanol, n-butanol, isobutanol, tert-butanol and the like; "chloro solvents" such as dichloromethane, chloroform, dichloroethane, carbon tetrachloride and the like; "nitrile solvents" such as acetonitrile, propionitrile, butyronitrile, isobutyronitrile and the like; polar solvents such as water and also mixtures thereof.

The term "suitable base" used herein the present invention until unless specified is selected from inorganic bases like "alkali metal hydroxides" such as lithium hydroxide, sodium hydroxide, potassium hydroxide and the like; "alkali metal carbonates" such as sodium carbonate, potassium carbonate, lithium carbonate and the like; "alkali metal bicarbonates" such as sodium bicarbonate, potassium bicarbonate, lithium bicarbonate and the like; "alkali metal hydrides" such as sodium hydride, potassium hydride, lithium hydride and the like; "alkali metal alkoxides" such as sodium methoxide, sodium ethoxide, sodium tert-butoxide, potassium methoxide, potassium ethoxide, potassium tert-butoxide and the like; ammonia; and organic bases such as triethyl amine, methyl amine, ethyl amine, 1,8-Diazabicyclo[5.4.0]undec-7-ene (DBU), 1,5-Diazabicyclo(4.3.0)non-5-ene (DBN), lithium dioisoporpylamide (LDA), n-butyl lithium, tribenzylamine, isopropyl amine, diisopropylamine, diisopropylethylamine, N-methylmorpholine, N-ethylmorpholine, piperidine, dimethylaminopyridine, morpholine, pyridine, 2,6-lutidine, 2,4,6-collidine, imidazole, 1-methylimidazole, 1,2,4-triazole, 1,4-diazabicyclo[2.2.2]octane (DABCO) or mixtures thereof.

The term "coupling agent" used herein the present invention refers to a reagent or a combination of reagents that facilitates formation of an amide bond between the acid and the amine. The suitable coupling agent is selected from alkyl (or) aryl chloroformates such as methyl chloroformate, ethyl chloroformate, isobutyl chloroformate, isopropenyl chloroformate, phenyl chloroformate, benzyl chloroformate, p-nitrophenyl chloroformate and the like; carbonyldiimidazole (CDI); carbonyl ditriazole; boron-containing acids such as boric acid, boronic acids; ketals such as 2,2-dimethoxypropane; carbodiimides such as dicyclohexyl carbodiimide (DCC), 1-(3-dimethylaminopropyl)-3-ethylcarbodiimide hydrochloride (EDC-hydrochloride), diisopropyl carbodiimide and the like; oxalyl chloride; diphenylphosphoroazidate (DPPA); $P_2O_5$; thionyl chloride, methane sulfonyl chloride, benzene sulfonyl chloride, toluene sulfonyl chloride, methane sulfonic anhydride, (Benzotriazol-1-yloxy) tris(dimethylamino)phosphoniumhexafluoro phosphate (BOP), (Benzotriazol-1-yloxy) tripyrrolidinophosphonium hexafluorophosphate (PyBOP), O-(7-azabenzotriazol-1-yl)-N,N,N',N'-tetramethyluronium hexafluoro phosphate (HATU).

The coupling reaction optionally includes the addition of catalyst such as 1-hydroxybenzotriazole (HOBt), 1-hydroxy-7-azatriazole (HOAt), 1-hydroxy-1H-1,2,3-triazole-4-carboxylate (HOCt), N-hydroxy succinimide (HOSu), (2-(1H-benzotriazol-1-yl)-1,1,3,3-tetramethyl uronium tetrafluoro borate (TBTU).

The first aspect of the present invention provides an improved process for the preparation of (R)-3-((S)-2-benzyl-3-hydroxypropanoyl)-4-phenyloxazolidin-2-one compound of formula-5, comprising of hydroxy methylating the (R)-4-phenyl-3-(3-phenylpropanoyl)oxazolidin-2-one compound of formula-4 with 1,3,5-trioxane in presence of a suitable base and a suitable catalyst in a suitable solvent provides (R)-3-((S)-2-benzyl-3-hydroxypropanoyl)-4-phenyloxazolidin-2-one compound of formula-5.

Wherein the suitable base is selected from organic base and suitable catalyst is titanium tetrachloride and suitable solvent is selected from ester solvents, chloro solvents, hydrocarbon solvents, ketone solvents and alcohol solvents or mixture thereof.

The preferred embodiment of the present invention provides an improved process for the preparation of (R)-3-((S)-2-benzyl-3-hydroxypropanoyl)-4-phenyloxazolidin-2-one compound of formula-5, comprising of hydroxy methylating the (R)-4-phenyl-3-(3-phenylpropanoyl)oxazolidin-2-one compound of formula-4 with 1,3,5-trioxane in presence of diisopropyl ethylamine and titanium tetrachloride in dichloromethane provides (R)-3-((S)-2-benzyl-3-hydroxypropanoyl)-4-phenyl oxazolidin-2-one compound of formula-5.

Another preferred embodiment of the present invention provides an improved process for the preparation of (R)-3-((S)-2-benzyl-3-hydroxypropanoyl)-4-phenyloxazolidin-2-one compound of formula-5, comprising of hydroxy methylating the (R)-4-phenyl-3-(3-phenylpropanoyl)oxazolidin-2-one compound of formula-4 with 1,3,5-trioxane in presence of triethylamine and titanium tetrachloride in dichloromethane provides (R)-3-((S)-2-benzyl-3-hydroxypropanoyl)-4-phenyl oxazolidin-2-one compound of formula-5.

The second aspect of the present invention provides an improved process for the preparation of (S)-2-benzyl-3-hydroxypropanoic acid compound of formula-1, comprising of:
  a) Hydroxy methylating the (R)-4-phenyl-3-(3-phenylpropanoyl)oxazolidin-2-one compound of formula-4 with 1,3,5-trioxane in presence of a suitable base and a suitable catalyst in a suitable solvent provides (R)-3-((S)-2-benzyl-3-hydroxy propanoyl)-4-phenyloxazolidin-2-one compound of formula-5,
  b) hydrolyzing the compound of formula-5 with a suitable base in the presence of hydrogen peroxide in a suitable solvent provides (S)-2-benzyl-3-hydroxypropanoic acid compound of formula-1.
Wherein,
in step-a) the suitable base, catalyst and solvent used are same as defined in the first aspect of the present invention;
in step-b) the suitable base is selected from inorganic base and suitable solvent is selected from alcohol solvents, ester solvents, ether solvents, chloro solvents and hydrocarbon solvents or mixture thereof.

The preferred embodiment of the present invention provides an improved process for the preparation of (S)-2-benzyl-3-hydroxypropanoic acid compound of formula-1, comprising of;
  a) Hydroxy methylating the (R)-4-phenyl-3-(3-phenylpropanoyl)oxazolidin-2-one compound of formula-4 with 1,3,5-trioxane in presence of diisopropyl ethylamine and titanium tetrachloride in dichloromethane provides (R)-3-((S)-2-benzyl-3-hydroxy propanoyl)-4-phenyloxazolidin-2-one compound of formula-5,
  b) hydrolyzing the compound of formula-5 with lithium hydroxide in presence of hydrogen peroxide in tetrahydrofuran provides (S)-2-benzyl-3-hydroxypropanoic acid compound of formula-1.

The preferred embodiment of the present invention provides an improved process for the preparation of (S)-2-benzyl-3-hydroxypropanoic acid compound of formula-1, comprising of;
  a) Hydroxy methylating the (R)-4-phenyl-3-(3-phenylpropanoyl)oxazolidin-2-one compound of formula-4 with 1,3,5-trioxane in presence of triethylamine and titanium tetrachloride in dichloromethane provides (R)-3-((S)-2-benzyl-3-hydroxy propanoyl)-4-phenyloxazolidin-2-one compound of formula-5,
  b) hydrolyzing the compound of formula-5 with lithium hydroxide in presence of hydrogen peroxide in tetrahydrofuran provides (S)-2-benzyl-3-hydroxypropanoic acid compound of formula-1.

The third aspect of the present invention provides an improved process for the preparation of (S)-2-benzyl-3-hydroxypropanoic acid compound of formula-1 or its phenylethylamine salt compound of formula-1a, comprising of the following steps:
  a) Reacting the 3-phenylpropanoic acid compound of formula-2 with (R)-4-phenyloxazolidin-2-one compound of formula-3 in presence of a suitable coupling agent and a suitable base in a suitable solvent provides (R)-4-phenyl-3-(3-phenyl propanoyl)oxazolidin-2-one compound of formula-4,
  b) hydroxy methylating the (R)-4-phenyl-3-(3-phenylpropanoyl)oxazolidin-2-one compound of formula-4 with 1,3,5-trioxane in the presence of a suitable base and a suitable catalyst in a suitable solvent provides (R)-3-((S)-2-benzyl-3-hydroxy propanoyl)-4-phenyloxazolidin-2-one compound of formula-5,
  c) hydrolyzing the compound of formula-5 with a base in the presence of hydrogen peroxide in a suitable solvent provides (S)-2-benzyl-3-hydroxypropanoic acid compound of formula-1,
  d) optionally, treating the compound of formula-1 with (S)-phenyl ethylamine in a suitable solvent provides (S)-phenyl ethylamine salt of (S)-2-benzyl-3-hydroxypropanoic acid compound of formula-1a and further converting it into compound of formula-1 by using a suitable acid in a suitable solvent.
Wherein,
in step-a) the suitable base is selected from organic base and suitable coupling agent is selected from dicyclohexyl carbodiimide (DCC), diisopropylcarbodiimide (DIC), ethyl-(N'',N''-dimethylamino)propyl carbodiimide hydrochloride (EDC), N, N-carbonyldiimidazole (CDI), DABAL-Me3, benzotriazolyloxytris(dimethylamino) phosphonium Hexafluoro phosphate (BOP), 2-(7-aza-1-H-benzotriazole-1-yl)-1,1,3,3-tetramethyluroniu hexafluorophosphate (HATU), benzotriazol-1-yl-N-oxy-tris(pyrrolidino)phosphonium hexafluoro phosphate (PyBOP), 7-azabenzotriazol-1-yl-N-oxy-tris(pyrrolidino)

phosphonium hexafluorophosphate (PyAOP) and suitable solvent is selected from chloro solvents, ether solvents, ester solvents, alcohol solvents and hydrocarbon solvents or mixture thereof;

in step-b) the suitable base, catalyst and solvent used are same as defined in the first aspect of the present invention;

in step-c) the suitable base and suitable solvent used are same as defined in the second aspect of the present invention;

in step-d) the suitable acid is selected from inorganic acid, preferably hydrochloric acid; and the suitable solvent is selected from chloro solvents, ether solvents, alcohol solvents, ester solvents, hydrocarbon solvents and polar solvents such as water or mixtures thereof.

The preferred embodiment of the present invention provides an improved process for the preparation of (S)-2-benzyl-3-hydroxypropanoic acid compound of formula-1 or its phenylethylamine salt compound of formula-1a, comprising of the following steps:

a) Reacting the 3-phenylpropanoic acid compound of formula-2 with (R)-4-phenyloxazolidin-2-one compound of formula-3 in presence of dicyclohexyl carbodiimide and dimethylaminopyridine in dichloromethane provides (R)-4-phenyl-3-(3-phenylpropanoyl) oxazolidin-2-one compound of formula-4, b) hydroxy methylating the (R)-4-phenyl-3-(3-phenylpropanoyl)oxazolidin-2-one compound of formula-4 with 1,3,5-trioxane in presence of triethylamine/diisopropyl ethylamine and titanium tetrachloride in dichloromethane provides (R)-3-((S)-2-benzyl-3-hydroxy propanoyl)-4-phenyloxazolidin-2-one compound of formula-5, c) hydrolyzing the compound of formula-5 with lithium hydroxide in presence of hydrogen peroxide in tetrahydrofuran provides (S)-2-benzyl-3-hydroxypropanoic acid compound of formula-1, d) treating the compound of formula-1 with (S)-phenyl ethylamine in isopropanol provides (S)-phenyl ethylamine salt of (S)-2-benzyl-3-hydroxypropanoic acid compound of formula-1a and further converting it into compound of formula-1 by treating it with hydrochloric acid in ethylacetate and water.

The fourth aspect of the present invention is to provide an improved process for the preparation of (R)-4-phenyl-3-(3-phenylpropanoyl)oxazolidin-2-one compound of formula-4, comprising of reacting the 3-phenylpropanoic acid compound of formula-2 with (R)-4-phenyloxazolidin-2-one compound of formula-3 in presence of a suitable coupling agent and a suitable base in a suitable solvent to provide (R)-4-phenyl-3-(3-phenylpropanoyl) oxazolidin-2-one compound of formula-4.

The preferred embodiment of the present invention provides an improved process for the preparation of (R)-4-phenyl-3-(3-phenylpropanoyl)oxazolidin-2-one compound of formula-4, comprising of reacting the 3-phenylpropanoic acid compound of formula-2 with (R)-4-phenyloxazolidin-2-one compound of formula-3 in presence of dicyclohexyl carbodiimide and dimethylaminopyridine in dichloromethane provides (R)-4-phenyl-3-(3-phenylpropanoyl)oxazolidin-2-one compound of formula-4.

The fifth aspect of the present invention is to provide an improved process for the preparation of Alvimopan dihydrate comprising of:

a) Reacting (S)-2-benzyl-3-hydroxypropanoic acid compound of formula-1 with ethyl 2-aminoacetate hydrochloride of formula-6 in presence of dicyclohexyl carbodiimide and triethylamine in dichloromethane provides (S)-ethyl 2-(2-benzyl-3-hydroxy propanamido)acetate compound of formula-7, b) treating the compound of formula-7 with methanesulfonyl chloride in presence of triethylamine in dichloromethane provides (S)-ethyl 2-(2-benzyl-3-(methylsulfonyloxy)propanamido)acetate compound of formula-8, c) reacting the compound of formula-8 with 3-((3R,4R)-3,4-dimethylpiperidin-4-yl)phenol compound of formula-9 in presence of triethylamine in acetonitrile provides ethyl 2-((S)-2-benzyl-3-((3R,4R)-4-(3-hydroxyphenyl)-3,4-dimethyl piperidin-1-yl)propanamido)acetate hydrochloride compound of formula-10, d) treating the compound of formula-10 with sodium hydroxide in aqueous ethanol provides Alvimopan dihydrate, e) optionally, purifying the obtained compound from a suitable solvent provides pure Alvimopan dihydrate.

We, the present inventors have in-toto repeated the process disclosed in U.S. Pat. No. 5,434,171 and characterized the PXRD pattern of the obtained Alvimopan dihydrate. The PXRD pattern of the Alvimopan dihydrate obtained from the present process is similar to the PXRD pattern obtained from the process disclosed in U.S. Pat. No. 5,434,171.

The sixth aspect of the present invention is to provide highly pure (S)-2-benzyl-3-hydroxypropanoic acid compound of formula-1 comprising of, treating the compound of formula-1 with (S)-phenyl ethylamine in a suitable solvent provides (S)-phenyl ethylamine salt of (S)-2-benzyl-3-hydroxypropanoic acid compound of formula-1a and further converting it into compound of formula-1 by using a suitable acid in a suitable solvent.

The preferred embodiment of the present invention provides highly pure (S)-2-benzyl-3-hydroxypropanoic acid compound of formula-1 comprising of, treating the compound of formula-1 with (S)-phenyl ethylamine in isopropanol provides (S)-phenyl ethylamine salt of (S)-2-benzyl-3-hydroxypropanoic acid compound of formula-1a and further converting it into compound of formula-1 by treating it with hydrochloric acid in ethylacetate and water.

The main advantage of the present invention involves the preparation of (S)-phenyl ethylamine salt of (S)-2-benzyl-3-hydroxypropanoic acid compound of formula-1a which enhances the purity of (S)-2-benzyl-3-hydroxypropanoic acid compound of formula-1 as well as the purity of the desired compound i.e., Alvimopan dihydrate.

The seventh aspect of the present invention provides a novel (R)-3-((S)-2-benzyl-3-hydroxypropanoyl)-4-phenyloxazolidin-2-one compound of formula-5 which is represented as below:

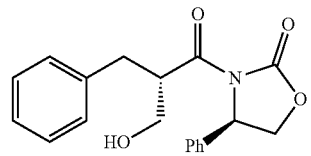

The present process for the preparation of (S)-2-benzyl-3-hydroxypropanoic acid compound of formula-1 involves the usage of (R)-4-phenyloxazolidin-2-one, which avoids the resolution of compound of formula-1 at the final stage and provides enantiomerically enriched desired compound of formula-1 in higher yields which avoids the loss of other isomer.

The eighth aspect of the present invention is to provide an alternate process for the preparation of Alvimopan dihydrate comprising of:

a) Treating the (S)-phenyl ethylamine salt of (S)-2-benzyl-3-hydroxypropanoic acid compound of formula-1a with hydrochloric acid in ethylacetate and water provides (S)-2-benzyl-3-hydroxypropanoic acid compound of formula-1 which on in-situ reacting with ethyl 2-aminoacetate hydrochloride of formula-6 in presence of dicyclohexyl carbodiimide and triethylamine in dichloromethane provides (S)-ethyl 2-(2-benzyl-3-hydroxypropanamido)acetate compound of formula-7, b) treating the compound of formula-7 with methanesulfonyl chloride in presence of triethylamine in ethylacetate provides (S)-ethyl 2-(2-benzyl-3-(methylsulfonyloxy)propanamido)acetate compound of formula-8, c) reacting the compound of formula-8 with 3-((3R,4R)-3,4-dimethylpiperidin-4-yl)phenol compound of formula-9 in presence of triethylamine in acetonitrile provides ethyl 2-((S)-2-benzyl-3-((3R,4R)-4-(3-hydroxyphenyl)-3,4-dimethyl piperidin-1-yl)propanamido)acetate hydrochloride compound of formula-10, d) treating the compound of formula-10 with sodium hydroxide in aqueous ethanol provides Alvimopan dihydrate, e) optionally, purifying the obtained compound from a suitable solvent provides pure Alvimopan dihydrate.

The novel (R)-3-((S)-2-benzyl-3-hydroxypropanoyl)-4-phenyloxazolidin-2-one compound of formula-5 of the present invention is useful in the preparation of (S)-2-benzyl-3-hydroxypropanoic acid compound of formula-1 or its phenylethylamine salt compound of formula-1a as well as in the preparation of Alvimopan dihydrate.

HPLC Method of Analysis:
(S)-phenyl ethylamine salt of (S)-2-benzyl-3-hydroxypropanoic acid compound of formula-1a Apparatus: A liquid chromatographic system equipped with variable wavelength UV-detector; Column: Kromasil C18 250× 4.6 mm, 5 μm or equivalent; Flow rate: 1.2 mL/min; Wavelength: 210 nm; Column Temperature: 25° C.; Injection volume: 10 μL; Run time: 60 min; Diluent: Methanol; Elution: Gradient; Buffer: Transfer accurately 1 mL of orthophosphoric acid (85%) in 1000 mL of Milli-Q-water and filter through 0.22μ Nylon membrane filter paper; Needle wash: Methanol; Mobile phase-A: Buffer (100%); Mobile phase-B: Acetonitrile:Water (90:10, v/v); Diluent: Acetonitrile:water (80:20, v/v).

Chiral Purity by HPLC:
(S)-phenyl ethylamine salt of (S)-2-benzyl-3-hydroxypropanoic acid compound of formula-1a Apparatus: A liquid chromatographic system equipped with variable wavelength UV-detector; Column: Chiral Pack IA, 250× 4.6 mm, 5μ or equivalent; Flow rate: 1.0 mL/min; Wavelength: 210 nm; Column Temperature: 25° C.; Injection volume: 10 μL; Run time: 30 min; Diluent: Methanol; Elution: Isocratic; Mobile phase: n-Hexane:Ethanol:Methanol:TFA (90:5:5:0.1%); Concentration: 2.0 mg/mL.

PXRD analysis of [[2(S)-[[4(R)-(3-hydroxyphenyl)-3(R),4-dimethyl-1-piperidinyl]methyl]-1-oxo-3-phenylpropyl]amino]acetic acid dihydrate produced by the present invention was carried out using BRUKER/AXS X-Ray diffractometer using Cu Kα radiation of wavelength 1.5406 A° and continuous scan speed of 0.03°/min.

Differential scanning calorimetric (DSC) analysis was performed with Q10 V9.6 Build 290 calorimeter. Samples of about 2 to 3 milligrams held in a closed pan were analyzed at a heating rate of 10° C. per minute.

The process of the present invention can be represented schematically as follows:

Scheme-I:

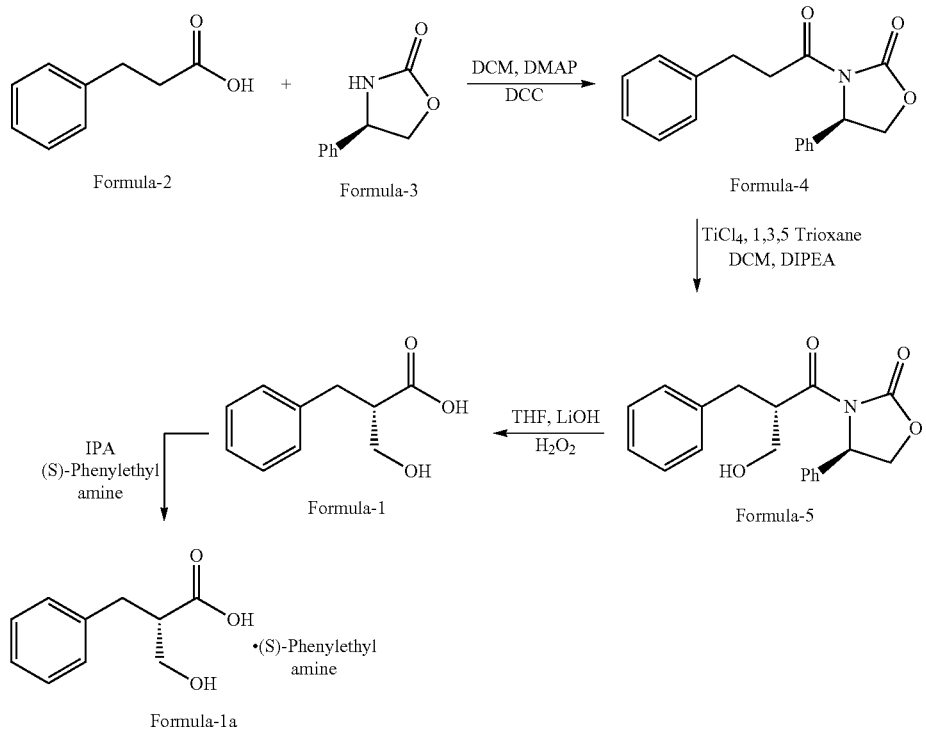

Scheme-II:

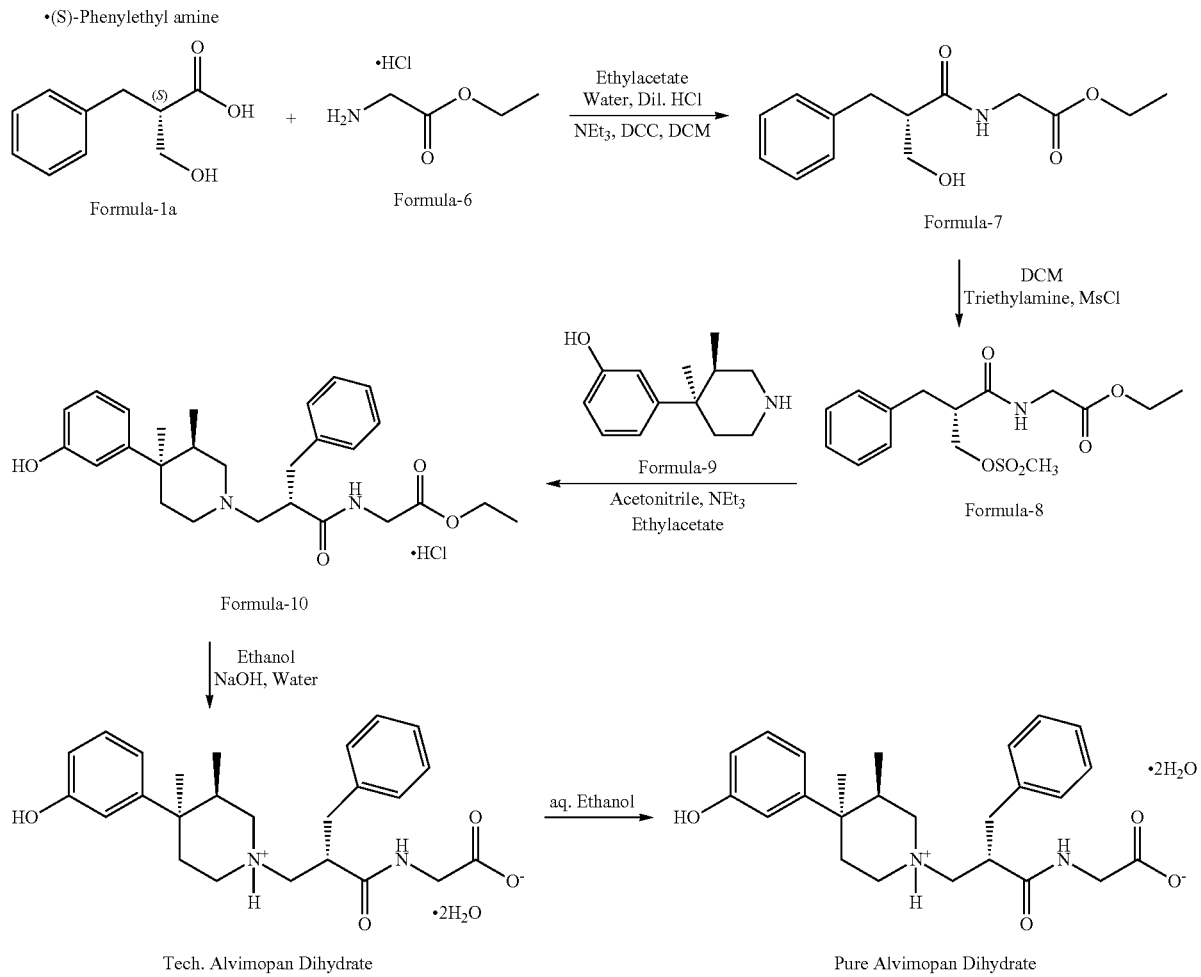

The process described in the present invention was demonstrated in examples illustrated below. These examples are provided as illustration only and therefore should not be construed as limitation of the scope of the invention.

EXAMPLES

Example-1: Preparation of (R)-4-phenyl-3-(3-phenylpropanoyl)oxazolidin-2-one (Formula-4)

A mixture of dichloromethane (3000 ml) and 3-phenylpropionic acid (200 gms) were stirred for 10 minutes at 25-30° C. (R)-4-phenyloxazolidin-2-one (213 gms) and dimethylamino pyridine (17.9 gms) were added to the above reaction mixture at 25-30° C. Cooled the reaction mixture to 10-15° C. Dicyclohexylcarbodiimide (288.5 gms) was added to the reaction mixture at 10-15° C. and stirred for 1 hour at the same temperature. Slowly raised the temperature of the reaction mixture to 25-30° C. and stirred for 2-3 hours at the same temperature. Filtered the reaction mixture and washed with dichloromethane. The filtrate was washed with hydrochloric acid solution and then followed by aqueous sodium bicarbonate solution. Distilled off the solvent completely from the organic layer and then co-distilled with isopropanol. To the obtained wet solid, isopropanol (700 ml) was added and then cooled the reaction mixture to 0-5° C. Stirred the reaction mixture for 1 hour at 0-5° C. Filtered the solid and washed with isopropanol and dried to get the title compound.

Yield: 326.5 gms; Melting point: 118-120° C. Purity by HPLC: 99.53%.

Example-2: Preparation of (R)-3-((S)-2-benzyl-3-hydroxypropanoyl)-4-phenyl oxazolidin-2-one (Formula-5)

A mixture of (R)-4-phenyl-3-(3-phenylpropanoyl)oxazolidin-2-one (100 gms) and dichloromethane (500 ml) was stirred for 10 minutes at 25-30° C. under nitrogen atmosphere. Cooled the reaction mixture to 0-5° C. Titanium tetrachloride (83.5 gms) was slowly added to the reaction mixture at 0-5° C. Further, diisopropyl ethylamine (55.14 gms) was added to the reaction mixture at 0-5° C. and stirred for 1 hour at the same temperature. Slowly 1,3,5-trioxane (61 gms) and then followed by titanium tetrachloride (83.5 gms) were added to the reaction mixture at 0-5° C. and stirred for 1 hour at the same temperature. Quenched the reaction mixture with aqueous ammonium chloride solution (ammonium chloride (200 gms) in water (1000 ml) at 0-5° C.). Both the organic and aqueous layers were separated and aqueous layer was extracted with dichloromethane. Combined the both organic layers and washed with water and followed by aqueous sodium chloride solution. Distilled off the solvent completely from the organic layer to get the title compound. Yield: 110 gms.

Example-3: Preparation of (S)-2-benzyl-3-hydroxypropanoic acid (Formula-1)

Tetrahydrofuran (500 ml) was added to (R)-3-((R)-2-benzyl-3-hydroxypropanoyl)-4-phenyloxazolidin-2-one obtained from example-2 at 25-30° C. and stirred for 15 minutes at the same temperature. Cooled the reaction mixture to 0-5° C. Hydrogen peroxide (46.06 ml) and then followed by lithium hydroxide (28.4 gms) were slowly added to the reaction mixture at 5-10° C. and stirred for 45 minutes at the same temperature. Slowly raised the temperature of the reaction mixture to 25-30° C. and stirred for 5-6 hours at the same temperature. Cooled the reaction mixture to 0-5° C. Quenched the reaction mixture with aqueous sodium sulphite solution (50 gms of sodium sulphite in 500 ml of water). Slowly raised the temperature of the reaction mixture to 25-30° C. and dichloromethane was added. Both the organic and aqueous layers were separated and washed the aqueous layer with dichloromethane. Acidifying the aqueous layer using dilute hydrochloric acid. Ethyl acetate was added to the reaction mixture at 25-30° C. and stirred the reaction mixture for 10 minutes at the same temperature. Both the organic and aqueous layers were separated and aqueous layer was extracted with ethyl acetate. Combined the both organic layers and washed with water. Distilled off the solvent from the organic layer under reduced pressure to get the title compound.

Yield: 53.0 gms; Purity by HPLC: 80.01%; Purity by chiral HPLC: 97.23%.

Example-4: Preparation of (S)-phenylethylamine (S)-2-benzyl-3-hydroxypropanoic acid (Formula-1a)

(S)-phenyl ethylamine (33.6 gms) was added to a mixture of (S)-2-benzyl-3-hydroxypropanoic acid (50 gms) and isopropanol (350 ml) at 25-30° C. Heated the reaction mixture to 80-85° C. and stirred for 15 minutes at the same temperature. Cooled the reaction mixture to 25-30° C. and stirred for 1-2 hours at the same temperature. Filtered the precipitated solid, washed with isopropanol and dried to get the title compound.

Yield: 56.5 gms; Melting point: 140-145° C. SOR: −19.374 (C=1 methanol); Purity by HPLC: 98.04%; Purity by chiral HPLC: 99.64%; Other isomer: 0.36%.

Example-5: Preparation of (R)-3-((S)-2-benzyl-3-hydroxypropanoyl)-4-phenyloxazolidin-2-one (Formula-5)

A mixture of (R)-4-phenyl-3-(3-phenylpropanoyl)oxazolidin-2-one (100 gms) and dichloromethane (500 ml) was stirred for 10 minutes at 25-30° C. under nitrogen atmosphere. Cooled the reaction mixture to 0-5° C. Titanium tetrachloride (83.5 gms) was slowly added to the reaction mixture at 0-5° C. Further, diisopropyl ethylamine (55.14 gms) was added to the reaction mixture at 0-5° C. and stirred for 1 hour at the same temperature. Slowly 1,3,5-trioxane (61 gms) and then followed by titanium tetrachloride (83.5 gms) were added to the reaction mixture at 0-5° C. and stirred for 1 hour at the same temperature. Quenched the reaction mixture with aqueous ammonium chloride solution (200 gms of ammonium chloride in 1000 ml of water) at 0-5° C. Both the organic and aqueous layers were separated and aqueous layer is extracted with dichloromethane. Combined the both organic layers and washed with water and followed by aqueous sodium chloride solution. The resulting organic layer was taken into the next step without isolation.

Example-6: Preparation of (S)-2-benzyl-3-hydroxypropanoic acid (Formula-1)

Tetrahydrofuran (500 ml) was added to organic layer obtained in example-5 at 25-30° C. and stirred for 15 minutes at the same temperature. Cooled the reaction mixture to 0-5° C. Hydrogen peroxide (46.06 ml) and then followed by lithium hydroxide (28.4 gms) were slowly added to the reaction mixture at 5-10° C. and stirred for 45 minutes at the same temperature. Slowly raised the temperature of the reaction mixture to 25-30° C. and stirred for 5-6 hours at the same temperature. Cooled the reaction mixture to 0-5° C. Quenched the reaction mixture with aqueous sodium sulphite solution (50 gms of sodium sulphite in 500 ml of water). Slowly raised the temperature of the reaction mixture to 25-30° C. and dichloromethane was added. Both the organic and aqueous layers were separated and washed the aqueous layer with dichloromethane. Acidifying the aqueous layer using dilute hydrochloric acid. Ethyl acetate was added to the aqueous layer at 25-30° C. and stirred the reaction mixture for 10 minutes at the same temperature. Both the organic and aqueous layers were separated and aqueous layer was extracted with ethyl acetate. Combined the both organic layers and washed with water. Distilled off the solvent from the organic layer under reduced pressure to get the title compound. Yield: 53.0 gms.

Example-7: Preparation of (S)-ethyl 2-(2-benzyl-3-(methylsulfonyloxy)propanamido) acetate (Formula-8)

A mixture of 1-phenylethanamine (S)-2-benzyl-3-hydroxypropanoate (140 gm), water (420 ml) and ethylacetate (420 ml) was stirred for 5 min at 25-30° C. Acidifying the reaction mixture by using dilute hydrochloric acid. Both the organic and aqueous layers were separated and the aqueous layer was extracted with ethyl acetate. Combined the organic layers and washed with water and distilled off the solvent completely from the organic layer. Dichloromethane (840 ml) and ethyl 2-aminoacetate hydrochloride (84.2 gm) was added to the obtained compound at 25-30° C. and stirred for 5 min at the same temperature. The reaction mixture was cooled to 10 to 15° C. Triethylamine (70.5 gm) followed by N,N'-dicyclocarbodiimide (115 gm) were slowly added to the reaction mixture at 10 to 15° C. and raised the temperature to 25-30° C. and stirred for 12 hours at the same temperature. Cooled the reaction mixture to 0 to 5° C. and stirred for 90 min at the same temperature. Filtered the unwanted by-product, washed with dichloromethane. Filtrate was washed with 5% aqueous hydrochloride solution followed by washed with aqueous sodium bicarbonate solution. Further, the organic layer was washed with water followed by saturated aqueous sodium chloride solution. Distilled off solvent completely under reduced pressure and co-distilled with ethylacetate. Ethylacetate (280 ml) was added to the obtained compound at 25-30° C. and stirred for 10 min. The reaction mixture was cooled to 0-5° C. and stirred for 30 minutes. Filtered the reaction mixture and washed with ethyl acetate. Distilled off solvent completely from the filtrate. Dichloromethane (840 ml) was added to the obtained compound. The reaction mixture was cooled to 10 to 15° C. Triethylamine (97.1 ml) and methane sulfonyl chloride (79.4 gm) were added to the reaction-mixture at 10-15° C. The reaction temperature was raised to 25-30° C. and stirred the reaction mixture for 2 hrs. Water was added to the reaction mixture and separated both the organic and aqueous layers. Aqueous layer was extracted with dichloromethane. Combined the organic layers and organic layer was washed with aqueous sodium carbonate solution. Distilled off the solvent completely under reduced pressure and co-distilled with tert butyl methyl ether. Tert butylmethylether (840 ml) was added to the obtained compound at 25-30° C. and stirred for 5 min at the same temperature. The reaction mixture was heated to reflux temperature and stirred for 10 minutes. The reaction mixture was slowly cooled to 0 to 5° C. and stirred for 30 minutes. Filtered the precipitated solid, washed with tert butyl methyl ether and dried to get the title compound. Yield: 118 gm; M.R: 74-79° C.

Example-8: Preparation of Ethyl 2-((S)-2-benzyl-3-((3R,4R)-4-(3-hydroxyphenyl)-3,4-dimethyl)piperidin-1-yl)propanamido)acetate hydrochloride (Formula-10)

A mixture of 3-((3R,4R)-3,4-dimethylpiperidin-4-yl)phenol (40 gm), (S)-Ethyl 2-(2-benzyl-3-(methoxysulfonyl)propanamido)acetate (66.9 gm) and acetonitrile (100 ml) was stirred for 15 min at 30° C. Triethylamine (40 ml) was added to the reaction mixture at 30° C. Heated the reaction mixture to 75-80° C. and stirred for 9 hrs at the same temperature. Reaction mixture was cooled to 25-30° C. (S)-Ethyl 2-(2-benzyl-3-(methoxysulfonyl) propanamido)acetate (20.7 gm) was added to the reaction mixture at 25 to 30° C. Heated the reaction mixture to 75-80° C. and stirred for 5 hrs at the same temperature. Reaction mixture was cooled to 25-30° C. Another lot of (S)-Ethyl 2-(2-benzyl-3-(methoxysulfonyl) propanamido)acetate (13.8 gm) was added to the reaction mixture at 25-30° C. Heated the reaction temperature to 75-85° C. and stirred for 8 hours at the same temperature. Distilled off solvent completely under reduced pressure from the reaction mixture. Water and ethylacetate were added to the obtained compound at 25-30° C. and stirred for 10 min. Both the organic and aqueous layers were separated. Aqueous layer was extracted with ethylacetate and combined the organic layers. Distilled off the solvent form the organic layer under reduced pressure. The obtained compound was purified by using column chromatography (cyclohexane: ethylacetate). Yield: 45 gm. Purity by HPLC: 93.97%; M.R: 94-100° C.

Example-9: Preparation of [[2(S)-[[4(R)-(3-hydroxyphenyl)-3(R), 4-dimethyl-1-piperidinyl]-1-oxo-3-phenylpropyl]amino]acetic acid dihydrate A mixture of ethyl 2-((S)-2-benzyl-3-((3R,4R)-4-(3-hydroxyphenyl)-3,4-dimethyl) piperidin-1-yl)propanamido) acetate hydrochloride (42 gm) and ethanol (840 ml) was stirred for 10 min at 30° C. Water (210 ml) was added to the reaction mixture at 25-30° C. Basifying the reaction mixture by using aqueous sodium hydroxide solution. Stirred the reaction mixture for 2 hours at 25-30° C. Filtered the reaction mixture through highflow bed and washed with 20% aqueous ethanol. The pH of the filtrate was adjusted to 6 using conc. HCl. Stirred the reaction mixture for 40 min at 25-30° C. Cooled the reaction mixture to 0 to 10° C. and stirred for 90 min at the same temperature. Filtered the solid, washed with water and dried to get the title compound. Yield: 26.3 gm; Purity by HPLC: 98.64%.

Example-10: Purification of [[2(S)-[[4(R)-(3-hydroxyphenyl)-3(R), 4-dimethyl-1-piperidinyl]-1-oxo-3-phenylpropyl]amino]acetic acid dihydrate A mixture of [[2(S)-[[4(R)-(3-hydroxyphenyl)-3(R) 4-dimethyl-1-piperidinyl]-1-oxo-3-phenylpropyl]amino]acetic acid dihydrate (25 gm), ethanol (525 ml) and water (150 ml) was stirred for 15 min at 25-30° C. Sodium hydroxide (1N) solution was added to the reaction mixture at 25-30° C. and stirred for 10 min at the same temperature. The pH of the reaction mixture was adjusted using conc. HCl. Stirred the reaction mixture for 2 hrs at 25-30° C. Filtered the precipitated solid and washed with water. The same procedure was repeated thrice. The obtained compound was dried to get the title compound. Yield: 10 gm Further, water (100 ml) was added to the resulting solid and stirred for 10 minutes. Sodium hydroxide (1N) solution was added to the reaction mixture at 30° C. and stirred for 10 min at the same temperature. The pH of the reaction mixture was adjusted using conc. HCl and stirred for 15 min at 30° C. Filtered the precipitated solid, washed with water and dried to get the title compound. Yield: 9.5 gm. Purity by HPLC: 99.60%

The P-XRD of the obtained compound is shown in FIG. 1.

Figure 2:
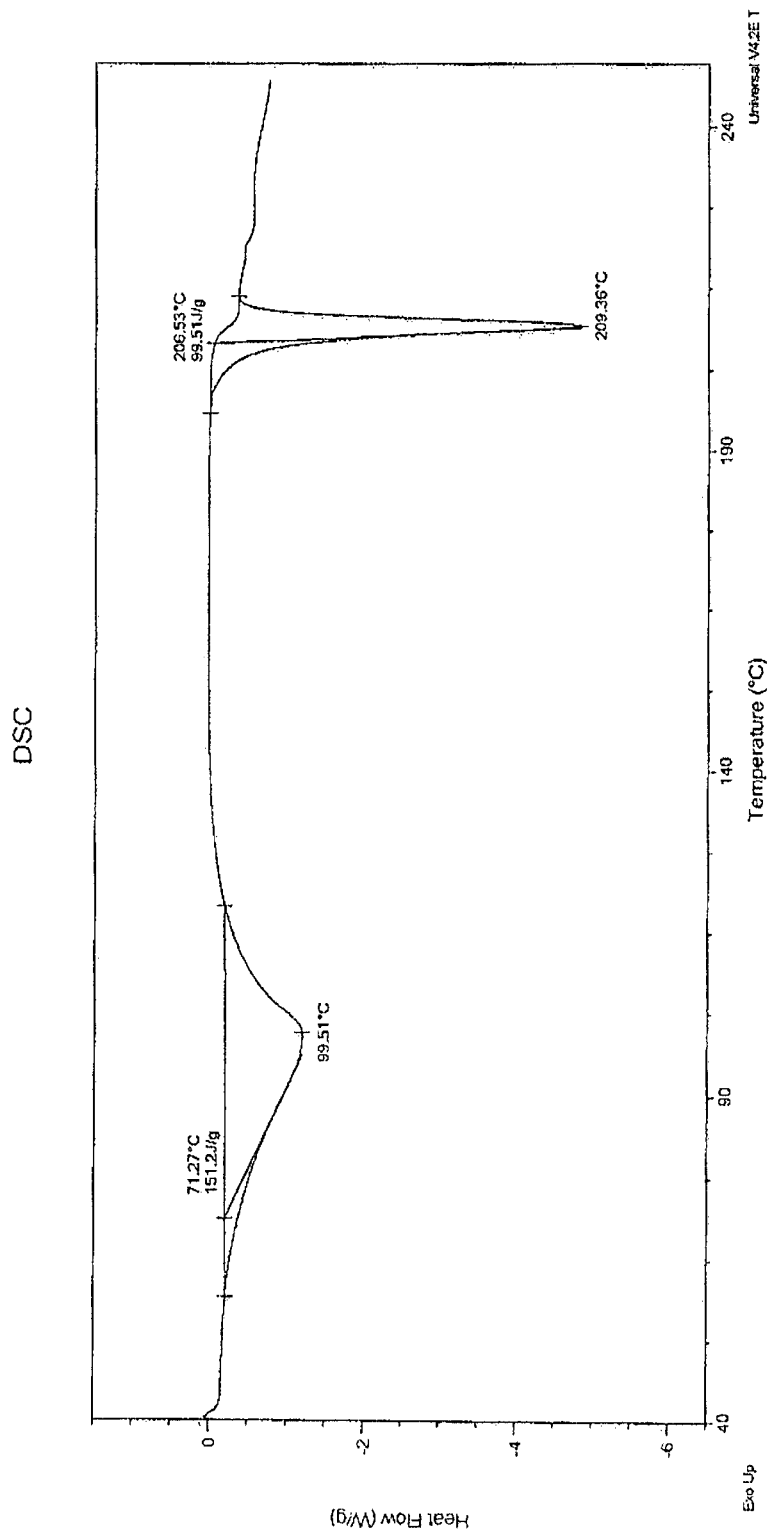
FIG. 2: Illustrates the DSC thermogram of crystalline form of [[2(S)-[[4(R)-(3-hydroxyphenyl)-3 (R),4-dimethyl-1-piperidinyl]methyl]-1-oxo-3-phenylpropyl]amino]acetic acid dihydrate.

The DSC thermogram of the obtained compound is shown in FIG. 2.

Example-11: Purification of [[2(S)-[[4(R)-(3-hydroxyphenyl)-3(R), 4-dimethyl-1-piperidinyl]-1-oxo-3-phenylpropyl]amino]acetic acid dihydrate A mixture of [[2(S)-[[4(R)-(3-hydroxyphenyl)-3(R) 4-dimethyl-1-piperidinyl]-1-oxo-3-phenylpropyl]amino]acetic acid dihydrate (23.5 gm) and water (235 ml) was stirred for 15 min at 25-30° C. 1N Sodium hydroxide (1N) solution was added to the reaction mixture at 25-30° C. and stirred for 10 min at the same temperature. The pH of the reaction mixture was adjusted using conc. HCl. Stirred the reaction mixture for 2 hrs at 30° C. Filtered the solid and washed with water and dried to get the title compound. Yield: 21.6 gm.

Example-12: Preparation of (R)-3-((S)-2-benzyl-3-hydroxypropanoyl)-4-phenyl oxazolidin-2-one (Formula-5)

A mixture of (R)-4-phenyl-3-(3-phenylpropanoyl)oxazolidin-2-one (100 gms) and dichloromethane (700 ml) were stirred for 15 minutes under nitrogen atmosphere at 25-30° C. Cooled the reaction mixture to 0-5° C. 1,3,5-trioxane (22.9 gms) and followed by triethyl amine (47.2 ml) were added to the reaction mixture at 0-5° C. Slowly titanium tetrachloride (192.7 gms) was added to the reaction mixture at 0-5° C. and stirred for 1 hour at the same temperature. The reaction mixture was added to aqueous ammonium chloride solution at 0-5° C. Stirred the reaction mixture for 15 minutes at 0-5° C. Both the organic and aqueous layers were separated. Aqueous layer was extracted with dichloromethane at 25-30° C. Combined the organic layers and washed with 20% aqueous ammonium chloride solution. 20% aqueous ammonia solution was added to the organic layer at 25-30° C. and stirred for 60 minutes at the same temperature. Both the organic layer and aqueous layer were separated and organic layer was washed with water. Distilled off the solvent and obtained compound was isolated by using column chromatography (cyclohexane:ethylacetate) to get the title compound. Yield: 120 gms. (m/z)=326.2 [M+H+]; M.R: 80-83° C.

Example-13: Preparation of (R)-4-phenyl-3-(3-phenylpropanoyl)oxazolidin-2-one (Formula-4)

A mixture of dichloromethane (2000 ml) and 3-phenylpropionic acid (200 gms) was stirred for 10 minutes at 25-30° C. (R)-4-phenyloxazolidin-2-one (212.9 gms), dimethylamino pyridine (16.2 gms) and dicyclohexylcarbodiimide (315.9 gms) were added to the reaction mixture at 25-30° C. and stirred for 5 hours at the same temperature. Cooled the reaction mixture to 0-5° C. and stirred for 1 V2 hour at the same temperature. Filtered the reaction mixture and washed with dichloromethane. The obtained filtrate was washed with 5% aqueous sodium carbonate solution. Organic layer was washed with water and then followed by 5% aqueous hydrochloric acid solution. Organic layer washed with water, distilled off the solvent completely under reduced pressure and then co-distilled with isopropanol. To the obtained compound, isopropanol (1000 ml) was added at 25-30° C. Heated the reaction mixture to 80-85° C. and stirred for 10 minutes at the same temperature. Cooled the reaction mixture to 0-5° C. and stirred for 2 hours at the same temperature. Filtered the precipitated solid, washed with isopropanol and dried to get the title compound.

Yield: 355. g gms; M. R: 125-127° C.; Purity by HPLC: 99.58%.

Example-14: Preparation of (S)-phenylethylamine (S)-2-benzyl-3-hydroxypropanoic acid (Formula-1a)

A mixture of (R)-4-phenyl-3-(3-phenylpropanoyl)oxazolidin-2-one (200 gms) and dichloromethane (1400 ml) were stirred for 10 minutes under nitrogen atmosphere at 25-30° C. Cooled the reaction mixture to 0-5° C. 1,3,5-trioxane (45.8 gms), triethyl amine (119 ml) and the followed by titanium tetrachloride solution ($TiCl_4$ 385.3 gms in dichloromethane 100 ml) were slowly added to the reaction mixture at 0-5° C. and stirred for 1 hour at the same temperature. The reaction mixture was slowly quenched into a pre-cooled aqueous ammonium chloride solution at 0-5° C. and stirred for 10 minutes at the same temperature. Both the organic and aqueous layers were separated and aqueous layer was extracted with dichloromethane. Total organic layer was washed with aqueous ammonium chloride solution. To the organic layer, aqueous ammonia solution was added at 25-30° C. and stirred for 1 hour at the same temperature. Both the organic and aqueous layers were separated and organic layer was washed with water. Distilled off the solvent completely under reduced pressure. Tetrahydrofuran (1000 ml) was added to the obtained compound at 25-30° C. and stirred for 15 minutes at the same temperature. Cooled the reaction mixture to 0-5° C. Hydrogen peroxide (92 ml) and followed by lithium hydroxide (28.4 gms) were slowly added to the reaction mixture at 0-5° C. and stirred for 2 hours at the same temperature. Quenched the reaction mixture using 10% aqueous sodium sulphite solution at 0-5° C. and stirred for 30 minutes at the same temperature. Raised the temperature of the reaction mixture to 25-30° C. Dichloromethane was added to the reaction mixture. Both the organic and aqueous layer were separated and aqueous layer was washed with dichloromethane. Expelled the aqueous layer aside for 30 minutes. Acidifying the aqueous layer using aqueous hydrochloric acid solution. Ethyl acetate was added to the reaction mixture at 25-30° C. and stirred for 10 minutes at the same temperature. Both organic and aqueous layers were separated and aqueous layer was extracted with ethyl acetate. Combined the organic layers and distilled off the solvent completely under reduced pressure. Isopropanol (700 ml) was added to the obtained compound at 25-30° C. and stirred for 10 minutes at the same temperature. (S)-1-phenyl ethylamine (73.85 gms) was added to the reaction mixture at 25-30° C. Heated the the reaction mixture to 80-85° C. and stirred for 15 minutes at same temperature. Cooled the reaction mixture to 25-30° C. and stirred for 2 hours at the same temperature. Filtered the solid and washed with isopropanol. To the obtained wet solid, isopropanol (700 ml) was added at 25-30° C. Heated the reaction to 80-85° C. and stirred for 15 minutes at the same temperature. Cooled the reaction mixture to 25-30° C. and stirred for 2 hours at the same temperature. Filtered the solid, washed with isopropanol and dried to get the title compound.

Yield: 123.8 gms; M.R: 152-156° C.; Purity by HPLC: 98.9%; Chiral Purity by HPLC: 99.97%.

Example-15: Preparation of Preparation of (S)-ethyl 2-(2-benzyl-3-(methylsulfonyloxy) propanamido) acetate (Formula-8)

A mixture of 1-phenylethanamine (S)-2-benzyl-3-hydroxypropanoate (100 gm), water (300 ml) and ethyl acetate (200 ml) were stirred for 5 min at 25-30° C. Acidified the reaction mixture using aqueous hydrochloric acid solution at 25-30° C. and stirred for 15 minutes at the same temperature. Both the organic and aqueous layers were separated and the aqueous layer was extracted with ethyl acetate. Combined the organic layers, washed with water and distilled off the solvent completely under reduced pressure. Dichloromethane (600 ml), ethyl 2-aminoacetate hydrochloride (60.2 gms), triethyl amine (50.36 gms) and N,N'-dicyclocarbodiimide (82.14 gms) were added to the obtained compound at 25-30° C. and stirred the reaction mixture for 6 hours at the same temperature. 10% aqueous hydrochloric acid was added to the reaction mixture. Cooled the reaction mixture to 0-5° C. and stirred for 2 hours at the same temperature. Filtered the reaction mixture and washed with dichloromethane. The obtained filtrate was washed with water and distilled off the solvent completely from the organic layer filtrate under reduced pressure. Ethyl acetate (200 ml) was added to the obtained compound. Cooled the reaction mixture to 0-5° C. and stirred for 1½ hour at the same temperature. Filtered the reaction mixture and washed with ethyl acetate. Cooled the obtained filtrate to 10-15° C. Triethylamine (67.15 gms) and methane sulfonyl chloride (57.01 gms) were added to the reaction mixture at 10-15° C. and stirred for 2 hours at the same temperature. Water was added to the reaction mixture an stirred for 15 minutes at 25-30° C. Both the organic and aqueous layers were separated and extracted the aqueous layer with ethyl acetate. Combined the organic layers and washed with aqueous sodium carbonate solution and then followed by aqueous hydrochloric acid solution. Organic layer was washed with water, distilled off the solvent completely under reduce pressure and then co-distilled with toluene. To the obtained compound, toluene (200 ml) was added at 25-30° C. Heated the reaction mixture to 60-65° C. and stirred for 15 minutes at the same temperature. Cooled the reaction mixture to 25-30° C. and stirred for 45 minutes at the same temperature. Cooled the reaction mixture to 0-5° C. and stirred for 1½ hour at the same temperature. Filtered the solid, washed with toluene and dried to get the title compound.

Yield: 80.1 gms; M.R: 74-79° C.; Purity by HPLC: 98.13%.

Reference Example-1: Preparation of [[2(S)-[[4(R)-(3-hydroxyphenyl)-3(R) 4-dimethyl-1-piperidinyl]-1-oxo-3-phenylpropyl]amino]acetic acid dihydrate according to U.S. Pat. No. 5,434,171

A mixture of Ethyl 2-((S)-2-benzyl-3-((3R,4R)-4-(3-hydroxyphenyl)-3,4-dimethyl) piperidin-1-yl)propanamido) acetate hydrochloride (5 gm) and ethanol (126 ml) was stirred for 10 min at 25-30° C. Water (29.6 ml) was added to the reaction mixture at 25-30° C. Sodium hydroxide (31.24 ml) was slowly added to the reaction mixture and stirred for 1 hr at the same temperature. The pH of the reaction mass was adjusted using conc. HCl. Stirred the reaction mixture for 2 hrs at 25-30° C. Filtered the solid, washed with water and dried to get the title compound. Yield: 3.2 gm.

The P-XRD of the obtained compound is shown in FIG. 1.

We claim:

1. A process for the preparation of (S)-2-benzyl-3-hydroxypropanoic acid compound of formula-1 or its phenylethylamine salt compound of formula-1a, comprising:
   (a) reacting the 3-phenylpropanoic acid compound of formula-2

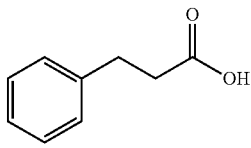

Formula-2 with (R)-4-phenyloxazolidin-2-one compound of formula-3

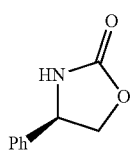

Formula-3 in presence of a suitable coupling agent and a suitable base in a suitable solvent to provide (R)-4-phenyl-3-(3-phenylpropanoyl)oxazolidin-2-one compound of formula-4,

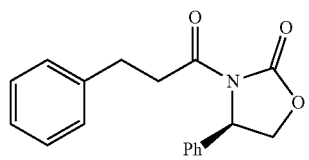

Formula-4

(b) hydroxy methylating the (R)-4-phenyl-3-(3-phenylpropanoyl) oxazolidin-2-one compound of formula-4 with 1,3,5-trioxane in the presence of a suitable base and a suitable catalyst in a suitable solvent to provide (R)-3-((S)-2-benzyl-3-hydroxy propanoyl)-4-phenyloxazolidin-2-one compound of formula-5,

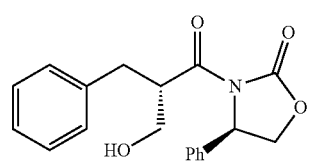 [SMILES: O=C1OC[C@@H](c2ccccc2)N1C(=O)[C@H](CO)Cc1ccccc1]

Formula-5

(c) hydrolyzing the compound of formula-5 with a base in the presence of hydrogen peroxide in a suitable solvent to provide (S)-2-benzyl-3-hydroxypropanoic acid compound of formula-1,

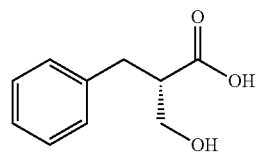

Formula-1

(d) optionally treating the compound of formula-1 with (S)-phenyl ethylamine in a suitable solvent to provide (S)-2-benzyl-3-hydroxypropanoic acid (S)-phenyl ethylamine salt compound of formula-1a and further treating the compound of formula-1a with a suitable acid in a suitable solvent to provide (S)-2-benzyl-3-hydroxypropanoic acid compound of formula-1.

2. The process according to claim 1, wherein,
   in step (a) the suitable base is dimethylaminopyridine and the suitable coupling agent is dicyclohexylcarbodiimide (DCC), and the suitable solvent is dichloromethane;
   in step (b) the suitable base is selected from triethyl amine or diisopropylethylamine; the suitable catalyst is titanium tetrachloride and the suitable solvent is dichloromethane;
   in step (c) the suitable base is lithium hydroxide and the suitable solvent is tetrahydrofuran
   in step (d) the suitable acid is aqueous hydrochloric acid; and a suitable solvent is selected from alcohol solvents, ester solvents, or polar solvents such as water or mixtures thereof.

3. The process according to claim 1, wherein the process of hydroxy methylating the (R)-4-phenyl-3-(3-phenylpropanoyl)oxazolidin-2-one compound of formula-4 with 1,3,5-trioxane to provide (R)-34(S)-2-benzyl-3-hydroxypropanoyl)-4-phenyl oxazolidin-2-one compound of formula-5 comprises diisopropylethylamine and titanium tetrachloride in dichloromethane.

4. The process according to claim 1, wherein the process for the preparation of formula-4 comprises reacting the 3-phenylpropanoic acid compound of formula-2 with (R)-4-phenyloxazolidin-2-one compound of formula-3 in presence of a suitable coupling agent selected from the group consisting of dicyclohexyl carbodiimide (DCC), diisopropylcarbodiimide (DIC), ethyl-(N",N"-dimethylamino)propyl carbodiimide hydrochloride (EDC), and N, N-carbonyldiimidazole (CDI), and a suitable base comprising an organic base in a suitable solvent selected from the group consisting of chloro solvents, ether solvents, ester solvents, alcohol solvents and hydrocarbon solvents or mixture thereof to provide (R)-4-phenyl-3-(3-phenylpropanoyl) oxazolidin-2-one compound of formula-4.

5. A process for the preparation of highly pure (S)-2-benzyl-3-hydroxypropanoic acid compound of formula-1, comprising:
   (a) treating the compound of formula-1 with (S)-phenyl ethylamine in a suitable solvent to provide (S)-phenyl ethylamine salt of (S)-2-benzyl-3-hydroxypropanoic acid compound of formula-1a, and
   (b) treating the compound of formula-1a with a suitable acid in a suitable solvent to provide highly pure compound of formula-1.

6. The process according to claim 1, wherein a process for the preparation of Alvimopan dihydrate comprising:
   a) reacting (S)-2-benzyl-3-hydroxypropanoic acid compound of formula-1 with ethyl 2-aminoacetate hydrochloride of formula-6 in presence of dicyclohexylcarbodiimide and triethylamine in dichloromethane to provide (S)-ethyl 2-(2-benzyl-3-hydroxy propanamido) acetate compound of formula-7,
   b) treating the compound of formula-7 with methanesulfonyl chloride in presence of triethylamine in dichloromethane to provide (S)-ethyl 2-(2-benzyl-3-(methylsulfony oxy)propanamido)acetate compound of formula-8,
   c) reacting the compound of formula-8 with 3-((3R,4R)-3,4-dimethylpiperidin-4-yl) phenol compound of formula-9 in presence of triethylamine in acetonitrile to provide ethyl 24-((S)-2-benzyl-3-((3R,4R)-4-(3-hydroxyphenyl)-3,4-dimethylpiperidin-1-yl) propanamido)acetate hydrochloride compound of formula-10,
   d) treating the compound of formula-10 with sodium hydroxide in aqueous ethanol to provide Alvimopan dihydrate, and
   e) optionally purifying the Alvimopan dihydrate by treating with aqueous sodium hydroxide in ethanol and followed by treating with conc. hydrochloric acid to provide pure Alvimopan dihydrate.

7. The process according to claim 1, wherein the chiral purity of (S)-2-benzyl-3-hydroxypropanoic acid is greater than 99.5%.

8. The process according to claim 1, wherein;
   in step (a) the coupling agent is dicyclohexyl carbodiimide and the base is dimethylaminopyridine and the solvent is dichloromethane;
   in step (b) the base is triethylamine, the catalyst is titanium tetrachloride, and the solvent is dichloromethane;
   in step (c) the base is lithium hydroxide and the solvent is tetrahydrofuran; and
   in step (d) the solvent is isopropanol, the acid is hydrochloric acid and the solvent is ethyl acetate and water.

9. The process according to claim 3, wherein the base is triethylamine, catalyst is titanium tetrachloride, and the solvent is dichloromethane.

10. The process according to claim 1, wherein the process for the preparation of (S)-2-benzyl-3-hydroxypropanoic acid compound of formula-1 comprises hydrolyzing the compound of formula-5 with lithium hydroxide in presence of hydrogen peroxide in tetrahydrofuran provides (S)-2-benzyl-3-hydroxypropanoic acid compound of formula-1.

11. A process for the preparation of Alvimopan dihydrate comprising:
   (a) treating the (S)-2-benzyl-3-hydroxypropanoic acid (S)-phenyl ethylamine salt compound of formula-1a with hydrochloric acid in a mixture of ethylacetate and water to provide (S)-2-benzyl-3-hydroxypropanoic acid compound of formula-1 which on in-situ reacting with ethyl 2-aminoacetate hydrochloride compound of formula-6 in presence of dicyclohexylcarbodiimide and triethylamine in dichloromethane to provide (S)-ethyl 2-(2-benzyl-3-hydroxypropanamido)acetate compound of formula-7,
   (b) treating the compound of formula-7 with methanesulfonyl chloride in presence of triethylamine in ethylacetate provides (S)-ethyl 2-(2-benzyl-3-(methylsulfonyloxy)propanamido)acetate compound of formula-8,
   (c) reacting the compound of formula-8 with 3-((3R,4R)-3,4-dimethylpiperidin-4-yl)phenol compound of formula-9 in presence of triethylamine in acetonitrile provides ethyl 24(S)-2-benzyl-3-((3R,4R)-4-(3-hydroxyphenyl)-3,4-dimethyl piperidin-1-yl)propanamido)acetate hydrochloride compound of formula-10,
   (d) treating the compound of formula-10 with sodium hydroxide in aqueous ethanol provides Alvimopan dihydrate, and
   (e) optionally purifying the Alvimopan dihydrate by treating with aqueous sodium hydroxide in ethanol and followed by treating with conc. hydrochloric acid to provide pure Alvimopan dihydrate.

12. The process according to claim 5, wherein a process for the preparation of highly pure (S)-2-benzyl-3-hydroxypropanoic acid compound of formula-1, comprises:
   in step (a), isopropanol as the solvent; and
   in step (b), hydrochloric acid as the acid and a mixture of ethylacetate and water as the solvent.

13. A compound having the structural formula of formula-5 according to claim 1.

* * * * *